(12) United States Patent
Iida et al.

(10) Patent No.: US 8,703,979 B2
(45) Date of Patent: Apr. 22, 2014

(54) PREPARATION OF ANTICANCER-ACTIVE TRICYCLIC COMPOUNDS VIA ALKYNE COUPLING REACTION

(75) Inventors: Akira Iida, Kyoto (JP); Kazunori Ueda, Kawachinagano (JP); Mitsuaki Yamashita, Takasaki (JP)

(73) Assignee: Taheebo Japan Co., Ltd., Osaka (JP)

( * ) Notice: Subject to any disclaimer, the term of this patent is extended or adjusted under 35 U.S.C. 154(b) by 0 days.

(21) Appl. No.: 13/190,799

(22) Filed: Jul. 26, 2011

(65) Prior Publication Data

US 2012/0077986 A1 Mar. 29, 2012

(30) Foreign Application Priority Data

Sep. 29, 2010 (JP) .................. 2010-218936
Mar. 8, 2011 (JP) .................. 2011-050363

(51) Int. Cl.
*C07D 307/92* (2006.01)
*A61K 31/343* (2006.01)

(52) U.S. Cl.
CPC ............. *C07D 307/92* (2013.01); *A61K 31/343* (2013.01)
USPC ......................................... 549/458; 514/468

(58) Field of Classification Search
CPC ............................ C07D 307/92; A61K 31/343
USPC ......................................... 549/458; 514/468
See application file for complete search history.

(56) References Cited

U.S. PATENT DOCUMENTS

| 5,663,197 | A | 9/1997 | Ueda et al. |
| 7,538,234 | B2 | 5/2009 | Iida et al. |
| 7,910,752 | B2 | 3/2011 | Tokuda et al. |
| 2008/0300415 | A1* | 12/2008 | Iida et al. ............... 549/458 |
| 2009/0042977 | A1 | 2/2009 | Tokuda et al. |

FOREIGN PATENT DOCUMENTS

| JP | 4-139177 | 5/1992 |
| JP | 4-211650 | 8/1992 |
| JP | 2669762 | 7/1997 |
| JP | 2006-290871 | 10/2006 |
| JP | 4077863 | 2/2008 |
| WO | WO 2004/026253 | 4/2004 |
| WO | WO 2006/098355 | 9/2006 |

OTHER PUBLICATIONS

Ueda et al. "Production of anti-tumour-promoting furano-naphthoquinones in *Tabebuia avellanedae* cell cultures". *Phytochemistry*, vol. 36. No. 2, pp. 323-325 (1994).

(Continued)

Primary Examiner — Robert Havlin

(74) Attorney, Agent, or Firm — Hamre, Schumann, Mueller & Larson, P.C.

(57) ABSTRACT

The present invention is directed to provide a novel preparation of anticancer-active tricyclic compounds via alkyne coupling reaction. The present invention provides a process for preparing a compound of formula (Ia) or (Ib):

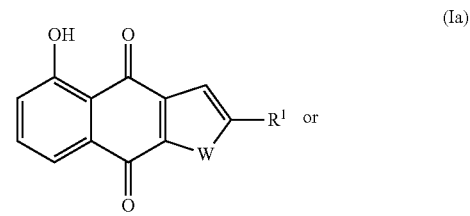

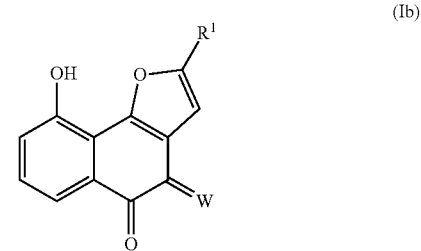

wherein $R^1$ is optionally substituted $C_{1-6}$ alkyl, etc.; W is O, S or $NR^2$; $R^2$ is hydrogen atom, etc.,
which comprises Step (a) in which a compound of formula (II):

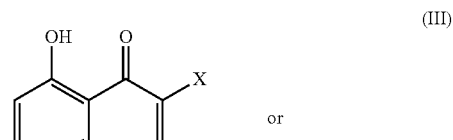

wherein $R^1$ is the same as defined above,
and a compound of formula (III) or (IV):

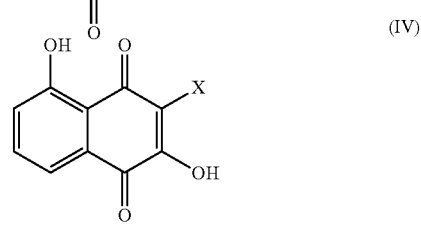

wherein $R^2$ is the same as defined above; $R^3$ is hydrogen atom, etc.; X is halogen atom, etc., are reacted in the presence of a base, a copper catalyst and a palladium catalyst in an aprotic polar solvent.

7 Claims, No Drawings

(56) References Cited

OTHER PUBLICATIONS

Romanov et al. "Substitution of acetylenic groups for halogen in the quinonoid ring". *Russian Chemical Bulletin*, International Edition, vol. 54, No. 7, pp. 1686-1689 (Jul. 2005).

Shvartsberg et al. "Acetylenic derivatives of quinones". *Russian Chemical Reviews*, vol. 73, No. 2, pp. 161-184 (2004).

Shvartsberg et al. "Synthesis of benz[f]indole-4,9-diones via acetylenic derivatives of 1,4-naphthoquinone". *Tetrahedron Letters*, vol. 50, pp. 6769-6771 (2009).

Chaker et al. "Studies on the Oxidative Addition of N, N-Dimethylamine to Bromojuglones and Bromomethyljuglones" *Chemical and Pharmaceutical Bulletin*, vol. 42, No. 11, pp. 2238-2240 (1994).

Kobayashi et al. One-Pot Synthesis of Naphtho[2, 3-*b*]furan-4,--diones by Sequential Coupling/Ring Closure Reactions *Tetrahedron Letters*, vol. 38, No. 5, pp. 837-840 (1997).

Cameron et al. "Reaction of 2-Acetoxy-3-chloro and 2, 3-Diacetoxy Naphthoquinones with 1,3-Dioxy and 1, 1, 3-Trioxy Butadienes" *Australian Journal of Chemistry*, vol. 52, No. 12, pp. 1165-1171 (1999).

Romanov et al. "Heterocyclization of N-Substituted 2-Amino-3-Acetylenyl-1, 4-Naphthoquinones" *Russian Chemical Bulletin*, vol. 34 pp. 994-997 (1985).

De Oliveria et al. "Lignans and Naphthoquinones from *Tabebuia incana*". *Phytochemistry*, vol. 34, No. 5, pp. 1409-1412 (1993).

Thomson. "Studies in the Juglone Series. II. Hydroxy and Hydroxyhalogeno Derivatives". *Journal of Organic Chemistry*, vol. 13, pp. 870-878 (1948).

* cited by examiner

PREPARATION OF ANTICANCER-ACTIVE TRICYCLIC COMPOUNDS VIA ALKYNE COUPLING REACTION

TECHNICAL FIELD

The present invention relates to a novel preparation of anticancer-active tricyclic compounds including naphthoquinones via alkyne coupling reaction.

BACKGROUND ART

It is known that naphthoquinones have various medicinal effects. For example, among naphthoquinones, (−)-2-(1-hydroxyethyl)-5-hydroxynaphtho[2,3-b]furane-4,9-dione, also referred to as NQ801 hereinafter, of the following formula:

[Chemical Formula 1]

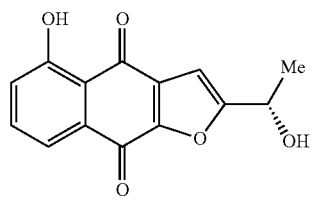

is an optically active compound comprised in Bignoniaceae Tabebuia, Taheebo, including *Tabebuia avellanedae; Tabebuia impetiginosa*, etc., and is known to have the anticancer activity (see Patent Document 1 and Nonpatent Document 1). Some methods for synthesizing NQ801 are known, and for example, include the following scheme (see Patent Documents 2 and 3):

[Chemical Formula 2]

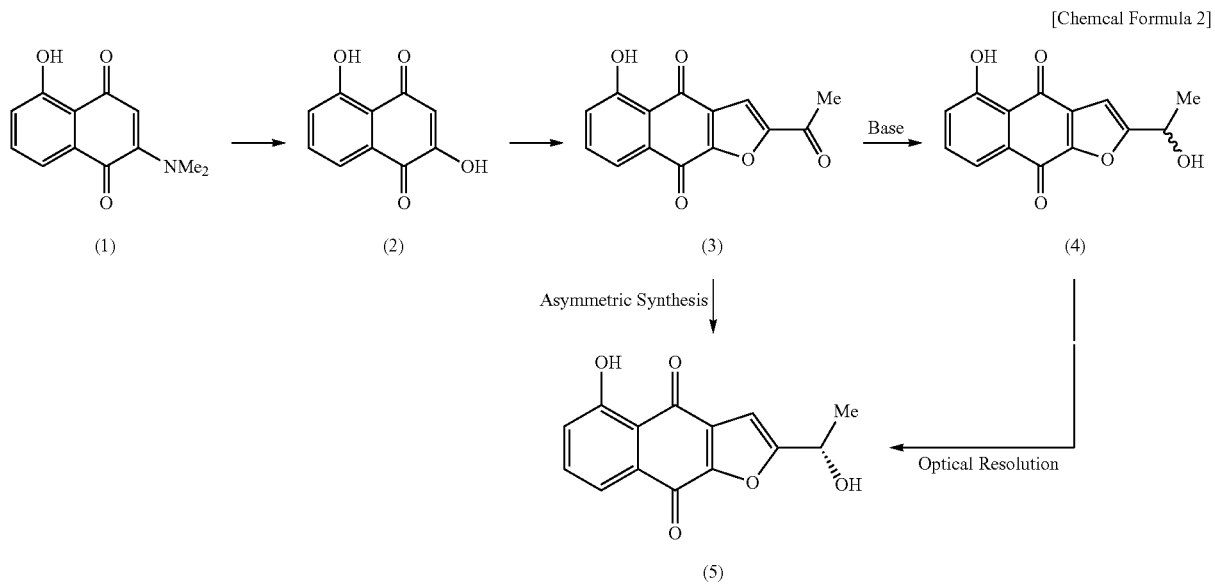 [SMILES: CN(C)C1=CC(=O)c2c(O)cccc2C1=O ; O=C1C(O)=CC(=O)c2c(O)cccc21 ; CC(=O)c1cc2c(o1)C(=O)c1cccc(O)c1C2=O ; CC(O)c1cc2c(o1)C(=O)c1cccc(O)c1C2=O ; C[C@H](O)c1cc2c(o1)C(=O)c1cccc(O)c1C2=O]

In the methods of both Patent Documents, 5-hydroxynaphtho[2,3-b]furane-4,9-dione (3) which is synthesized from 2-dimethylamino-5-hydroxynaphthalene-1,4-dione (1) derived from easily available 5-hydroxynaphthalene-1,4-dione, also referred to as juglone hereinafter, is used as a key intermediate. In the above methods, nonnegligible amounts of by-product (3') are obtained in a step wherein the key intermediate (3) is synthesized from the above compound (2), and it is not easy to separate the by-product from the compound (3).

[Chemical Formula 3]

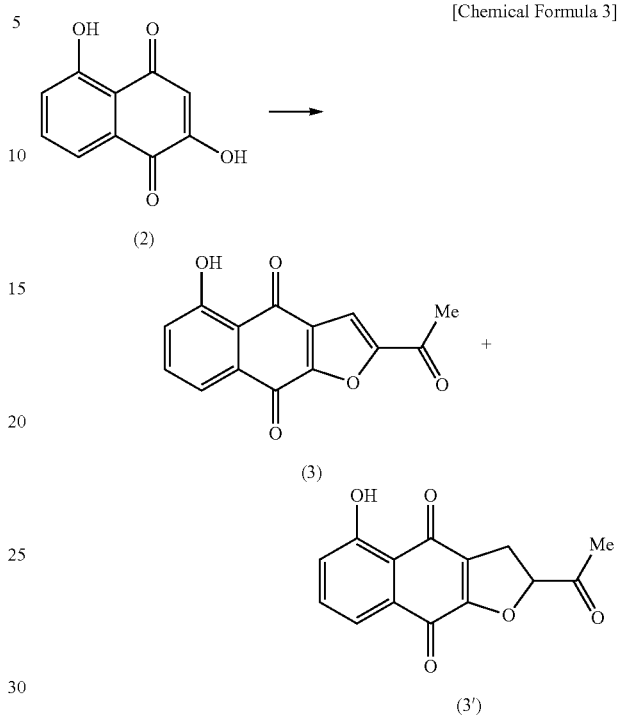

In the method of Patent Document 2, it is required that the desired compound (3) is reduced by a base, and then the resulting racemate (4) of NQ801 is optically resolved. In the method of Patent Document 3, the number of synthetic steps is reduced by an asymmetric synthesis compared to the method of Patent Document 2, but a problem which the compound (3) has to be separated from the by-product (3') produced in the synthesis still remains.

On the other hand, it is known that naphthopyrrole-diones are synthesized by the conventional Sonogashira coupling reaction using the similar substrate to the above compound (1) like the following scheme (see Nonpatent Document 2):

[Chemical Formula 4]

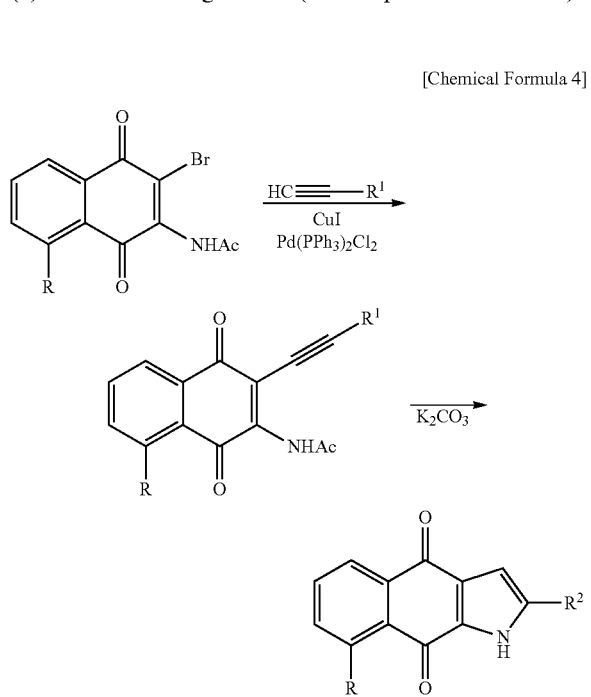

However, the method of the above literature wherein the substituent R of benzene ring is low reactive and comparatively stable chemical group is specific to the substrate. Since the alkyne is required to be treated in a ring-closure reaction in other step after the coupling reaction in the synthesis of naphthopyrrole-diones in the above method, a problem in view of the number of synthetic steps remains.

Furthermore, the following reaction is known as the coupling reaction of naphthoquinones and alkynes (see Nonpatent Document 3):

[Chemical Formula 5]

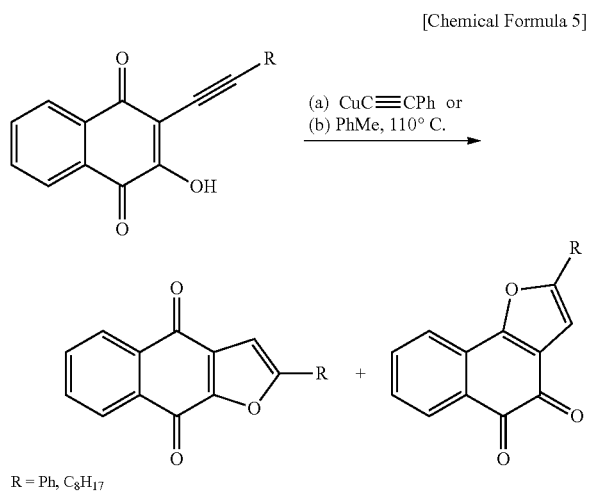

R = Ph, C$_8$H$_{17}$

In the method of Nonpatent Document 3, two types of naphthofuranediones are nonselectively obtained and no methods wherein either one of naphthofuranediones may be selectively prepared are disclosed.

[Chemical Formula 6]

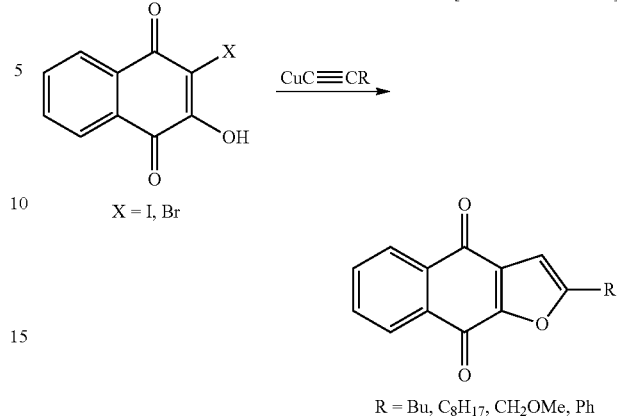

X = I, Br

R = Bu, C$_8$H$_{17}$, CH$_2$OMe, Ph

It is considered that hydroxyl group on 2-position of the naphthoquinone ring of the reaction substrate largely involves in the reaction disclosed in the literature.

Nonpatent Document 4 also discloses similar coupling reactions to the above, however, no reaction examples wherein a reaction substrate having hydroxyl group on 5-position of the naphthoquinone ring is used are disclosed.

[Patent Document 1] JP2669762
[Patent Document 2] JP-A-2006-290871
[Patent Document 3] JP4077863
[Nonpatent Document 1] Shinichi U E D A, et al., Phytochemistry (1994), Vol. 36, No. 2, p. 323-325
[Nonpatent Document 2] Mark S. Shvartsberg, et al., Tetrahedron Letters, 50 (2009), p. 6769-6771
[Nonpatent Document 3] S. Shvartsberg, et al., Russian Chemical Review 73(2), p. 161-184 (2004)
[Nonpatent Document 4] V. S. Romanov, et al., Russian Chemical Bulletin, International Edition, Vol. 54, No. 7, pp. 1686-1689

DISCLOSURE OF INVENTION

Problems to be Resolved by the Invention

The present invention is directed to provide a novel preparation of tricyclic compounds which is widely applicable to naphthoquinones including the anticancer-active ingredient NQ801. The present invention is also directed to provide a novel preparation wherein the reduced number of steps compared to the conventional methods allows for efficient and industrial productions of tricyclic compounds. The present invention is further directed to provide a novel and selective preparation of tricyclic compounds having different structures.

Means of Solving the Problems

The present invention provides the following embodiments:

[1] A process for preparing a compound of formula (Ia) or (Ib):

[Chemical Formula 7]

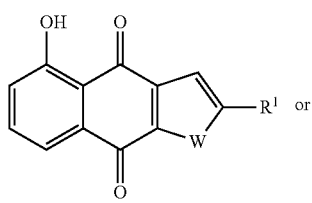

(Ia)

-continued (Ib)

wherein R¹ is selected from the group consisting of hydrogen atom; $C_{1-6}$ alkyl optionally substituted by hydroxy, $C_{1-6}$ alkoxy or amino; $C_{5-10}$ aryl optionally substituted by hydroxy, $C_{1-6}$ alkoxy or amino; 5- to 10-membered saturated or unsaturated heterocycle optionally substituted by hydroxy, $C_{1-6}$ alkoxy or amino; CHO; $CONH_2$; $C_{1-6}$ alkylcarbonyl optionally substituted by hydroxy, $C_{1-6}$ alkoxy or amino and $COC_{5-10}$ aryl optionally substituted by hydroxy, $C_{1-6}$ alkoxy or amino;

W is O, S or $NR^2$;

R² is selected from the group consisting of hydrogen atom; $C_{1-6}$ alkyl optionally substituted by nitro, sulfo, cyano, acetyl or $C_{5-10}$ aryl; $COC_{1-6}$ alkyl; and $COC_{5-10}$ aryl optionally substituted by nitro, sulfo, cyano or acetyl, which comprises Step (a) in which a compound of formula (II):

[Chemical Formula 8]

$$HC\equiv\!\!\!-R^1 \quad (II)$$

wherein R¹ is the same as defined above,
and a compound of formula (III) or (IV):

[Chemical Formula 9]

(III)

or (IV)

wherein R² is the same as defined above;

R³ is selected from the group consisting of hydrogen atom; $C_{1-6}$ alkyl optionally substituted by nitro, sulfo, cyano, acetyl or $C_{5-10}$ aryl; $COC_{1-6}$ alkyl; and $COC_{5-10}$ aryl optionally substituted by nitro, sulfo, cyano or acetyl;

X is a halogen atom selected from the group consisting of chlorine, bromine and iodine; or $OSO_2CF_3$, are reacted in the presence of a base, a copper catalyst and a palladium catalyst in an aprotic polar solvent.

[2] The process of [1], wherein the copper catalyst used in Step (a) is copper (I) oxide.

[3] The process of [2], wherein R¹ is hydroxy-substituted $C_{1-6}$ alkyl.

[4] The process of any one of [1] to [3], which further comprises Step (b) in which a compound of formula (V):

[Chemical Formula 10]

(V)

wherein each symbol is the same as defined in [1],
which is obtained using a compound of formula (III) in Step (a) is cyclized.

[5] A process for preparing a compound of formula (Ia):

[Chemical Formula 11]

(Ia)

wherein each symbol is the same as defined in [1], of any one of [1] to [4], wherein the palladium catalyst is less than 5 mol % of palladium catalyst to a compound of formula (II) or (IV).

[6] A process for preparing a compound of formula (Ib):

[Chemical Formula 12]

(Ib)

wherein each symbol is the same as defined in [1], of any one of [1] to [4], wherein the palladium catalyst is 5 mol % or more of palladium catalyst to a compound of formula (III) or (IV).

[7] A compound of formula (Ia):

[Chemical Formula 13]

(Ia)

wherein each symbol is the same as defined in [1], obtained in the process of any one of [1] to [5].

[8] A compound of formula (Ib):

[Chemical Formula 14]

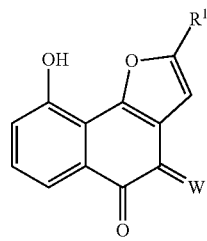

(Ib)

wherein each symbol is the same as defined in [1], obtained in the process of any one of [1] to [4], or [6].

[9] A compound of formula (III):

[Chemical Formula 15]

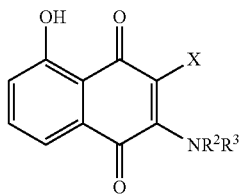 [SMILES: CNC1=C(Br)C(=O)c2c(O)cccc2C1=O]

(III)

wherein each symbol is the same as defined in [1].

[10] A compound of formula (IV):

[Chemical Formula 16]

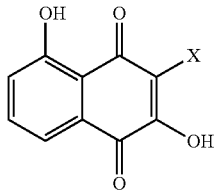

(IV)

wherein each symbol is the same as defined in [1].

[11] A compound of formula (V):

[Chemical Formula 17]

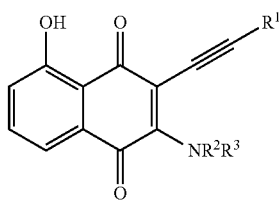

(V)

wherein each symbol is the same as defined in [1].

[12] The process of any one of [1] to [6], wherein both the base and the aprotic polar solvent used in Step (a) are pyridine.

Effect of Invention

In the present invention, one or more steps may be reduced compared to the conventional methods by comprising a step wherein 2,3-disubstituted naphthoquinone derivatives are reacted with alkyne compounds, and the desired tricyclic compounds may be efficiently and industrially produced.

In the present invention, the desired tricyclic compounds may be selectively prepared by adjusting the reaction condition of the step wherein the 2,3-disubstituted naphthoquinone derivatives are reacted with the alkyne compounds.

BEST MODE FOR CARRYING OUT THE INVENTION

The term "$C_{1-6}$ alkyl" used herein refers to a straight or branched chain saturated hydrocarbon having 1 to 6 carbons. A preferable "$C_{1-6}$ alkyl" includes methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, etc. A preferable "substituted $C_{1-6}$ alkyl" includes hydroxy-substituted $C_{1-6}$ alkyl such as 1-hydroxyethyl, benzyl, etc.

The "$C_{1-6}$ alkyl" moiety of the term "$C_{1-6}$ alkoxy" used herein has the same meaning as the above "$C_{1-6}$ alkyl". A preferable "$C_{1-6}$ alkoxy" includes methoxy, ethoxy, propoxy, isopropoxy, butoxy, isobutoxy, sec-butoxy, tert-butoxy, etc.

A preferable "$COC_{1-6}$ alkyl" used herein includes acetyl, etc.

The term "$C_{5-10}$ aryl" used herein refers to an aromatic hydrocarbon having 5 to 10 carbons. A preferable "$C_{5-10}$ aryl" includes phenyl, 1-naphthyl, 2-naphthyl, etc.

A preferable "$COC_{5-10}$ aryl" used herein includes benzoyl, etc.

The term "heterocycle" used herein includes monocyclic or multicyclic heterocycle, etc., and contains the same or different 1 or more heteroatoms selected from nitrogen atom, sulfur atom or oxygen atom. A preferable "heterocycle" includes aziridyl, azetidyl, pyrrolidyl, piperidyl, pyrrolyl, thienyl, benzothienyl, benzofuranyl, benzoxazolyl, benzthiazolyl, furyl, oxazolyl, thiazolyl, isooxazolyl, imidazolyl, pyrazolyl, pyridyl, pyradyl, pyrimidyl, pyridazyl, quinolyl, isoquinolyl, triazolyl, triazinyl, tetrazolyl, indolyl, imidazo[1,2-a]pyridyl, dibenzofuranyl, benzimidazolyl, quinoxalyl, cinnolyl, quinazolyl, indazolyl, naphthyridyl, quinolinolyl, isoquinolinolyl, etc.

The term "halogen atom" used herein includes chlorine atom, bromine atom, iodine atom, etc. A preferable halogen atom is bromine atom or iodine atom.

The term "aprotic polar solvent" used herein includes dimethylformamide (DMF), dimethylsulfoxide (DMSO), N-methylpyrrolidone (NMP), dimethylacetamide (DMA), tetrahydrofuran (THF), acetonitrile, acetone, pyridine, 4-methylpyridine, 2,4-dimethylpyridine, etc. A preferable aprotic polar solvent is DMF, DMSO or pyridine.

The terms of "the first aprotic polar solvent" and "the second aprotic polar solvent" used herein are each independently selected from the above aprotic polar solvent.

The term "copper catalyst" used herein includes a monovalent copper catalyst, preferably copper (I) oxide or copper (I) iodide, more preferably copper (I) oxide. The selection of the appropriate copper catalyst is one of the important factors for the progression of the desired reaction in the present preparation.

The term "palladium catalyst" used herein includes tetrakis (triphenylphosphine)palladium (0), dichlorobis(triphenylphosphine)palladium (II), diacetoxypalladium (II), also referred to as palladium acetate hereinafter, etc. preferably a divalent palladium catalyst, more preferably diacetoxypalladium (II). The types and concentrations of the appropriate palladium catalyst are one of the important factors for the progression of the desired reaction in the present preparation.

The term "base" used herein includes amine compounds, preferably pyridine, 4-methylpyridine, 2,4-dimethylpyridine, triethylamine, diethylamine, more preferably pyridine. When pyridine, 4-methylpyridine or 2,4-dimethylpyridine is used as the base, pyridine, 4-methylpyridine or 2,4-dimethylpyridine also works as the aprotic polar solvent.

The compounds of formulae (Ia) and (Ib) may be selectively synthesized by the adoption of the appropriate preparation conditions in the present preparation.

Specifically, a compound of formula (Ia) may be selectively prepared when the palladium catalyst is less than 5 mol %, preferably 1 to 3 mol %, to a compound of formula (III) or (IV).

A compound of formula (Ib) may be selectively prepared when the palladium catalyst is 5 mol % or more, preferably 6 to 10 mol %, to a compound of formula (III) or (IV).

The tricylic compounds prepared by the present invention may have at least one asymmetric carbon atom. Therefore, the present invention may produce not only racemates but also optically active substances thereof.

The preparation of a compound of formula (Ia) or (Ib) in the present invention is illustrated by examples, but is not limited thereto. The following abbreviations may be used herein for the sake of shorthand.

Me: methyl
Et: ethyl
Ac: acetyl
Ph: phenyl
THP: tetrahydropyranyl
NBS: N-bromosuccinimide
THF: tetrahydrofuran
DMF: dimethylformamide
DMSO: dimethylsulfoxide
NMP: N-methylpyrrolidone
DMA: dimethylacetamide Specific embodiments of the present invention are shown in the following Schemes A to D.

Scheme A: Preparation of Tricyclic Compounds

[Chemical Formula 18]

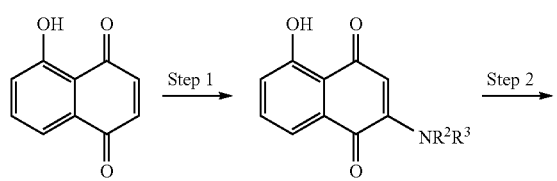

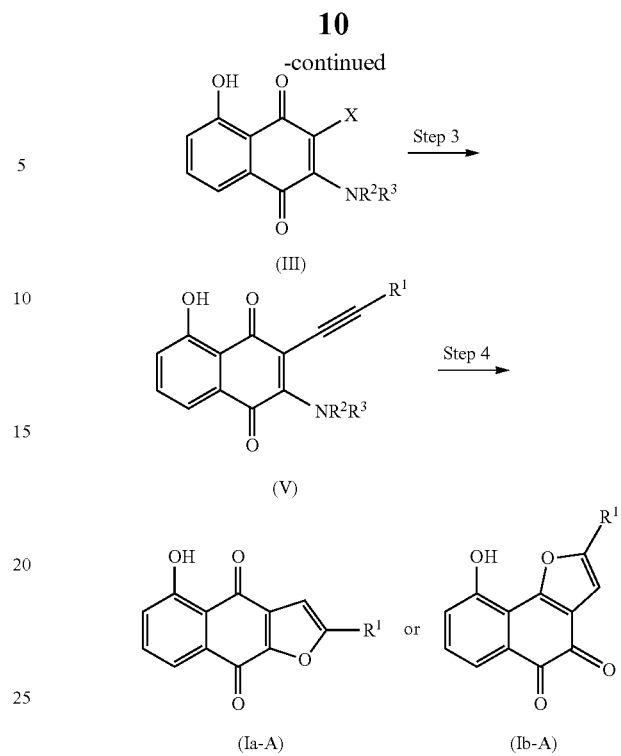

[In the Scheme, $R^1$ is selected from the group consisting of hydrogen atom; $C_{1-6}$ alkyl optionally substituted by hydroxy, $C_{1-6}$ alkoxy or amino; $C_{5-10}$ aryl optionally substituted by hydroxy, $C_{1-6}$ alkoxy or amino; 5- to 10-membered saturated or unsaturated heterocycle optionally substituted by hydroxy, $C_{1-6}$ alkoxy or amino; CHO; $CONH_2$; $C_{1-6}$ alkylcarbonyl optionally substituted by hydroxy, $C_{1-6}$ alkoxy or amino; and $COC_{5-10}$ aryl optionally substituted by hydroxy, $C_{1-6}$ alkoxy or amino;

$R^2$ and $R^3$ are each independently selected from the group consisting of hydrogen atom; $C_{1-6}$ alkyl optionally substituted by nitro, sulfo, cyano, acetyl or $C_{5-10}$ aryl; $COCl_{1-6}$ alkyl; and $COC_{5-10}$ aryl optionally substituted by nitro, sulfo, cyano or acetyl;

X is a halogen atom selected from the group consisting of chlorine, bromine and iodine, or $OSO_2CF_3$.]

Step 1 in the above Scheme A may be carried out according to Chaker, L.; Pautet, F.; Pillion, H., Chem. Pharm. Bull., 1994, 42, 2238-2240. In Step 1, to 5-hydroxynaphthalene-1,4-dione (also referred to as juglone hereinafter; for example, available from Tokyo Chemical Industry Co., Ltd.) dissolved in the appropriate solvent is added amine (i.e., $HNR^2R^3$) in neat or as a solution in an appropriate solvent. The solvent of juglone may be any organic solvents without any limitation, preferably toluene. A preferable solvent of amine is water, hexane, tetrahydrofuran, diethylether, toluene, methanol or ethanol. The reaction of Step 1 may be carried out at −78° C. to the reflux temperature of the solvent, preferably at the range of −40° C. to room temperature. Particularly, the reaction temperature from −40° C. to 0° C. is favorable in terms of the selectivity and the ease of operations.

Juglone is described in details in Merck Index, 13rd Ed., page 5288 and references cited therein.

In Step 2 of the above Scheme A, aminonaphthoquinone derivatives obtained in Step 1 are halogenated according to the conventional methods in the art. The halogenating agent includes N-bromosuccinimide, bromine, hydrogen bromide, iodine, hydrogen iodide, chlorine, hydrogen chloride, preferably N-bromosuccinimide.

In the alternative method of Step 2, a leaving group may be introduced as substituent X. The leaving group includes any groups acceptable for the next Steps 3 and/or 4, for example $OSO_2CF_3$.

In Step 3 of the above Scheme A, alkyne, the substituted aminonaphthoquinone derivative (III) obtained in Step 2 and a palladium catalyst are reacted in the presence of a copper catalyst and a base in the aprotic polar solvent to give an alkyne adduct (V). The preferable aprotic polar solvent is DMF or pyridine in the step. When pyridine is used as the base in the step, pyridine also works as the aprotic polar solvent.

In Step 3, 1 equivalent of the substrate compound (III) is reacted with excess equivalents, specifically 1 or more equivalents, preferably 5 to 10 equivalents, more preferably 10 equivalents of the reaction compound (i.e., alkyne).

Various alkyne compounds may be used as the alkyne in Step 3, preferably optionally substituted terminal alkyne. The substituent includes $C_{1-6}$ alkyl optionally substituted by hydroxy, $C_{1-6}$ alkoxy or amino; $C_{5-10}$ aryl optionally substituted by hydroxy, $C_{1-6}$ alkoxy or amino; 5- to 10-membered saturated or unsaturated heterocycle optionally substituted by hydroxy, $C_{1-6}$ alkoxy or amino; CHO; $CONH_2$; $C_{1-6}$ alkylcarbonyl optionally substituted by hydroxy, $C_{1-6}$ alkoxy or amino; and $COC_{5-10}$ aryl optionally substituted by hydroxy, $C_{1-6}$ alkoxy or amino, preferably hydroxy-substituted $C_{1-6}$ alkyl, more preferably 1-hydroxyethyl. In Step 3, optically active naphthoquinones may be prepared by using terminal alkynes having asymmetric carbon atoms.

Since the substituted aminonaphthoquinone derivative (III) is substituted by electron-donating hydroxyl group and may contain electron-donating amino group, it is generally considered that a coupling reaction of such a compound with alkyne hardly proceeds. However, the substituted aminonaphthoquinone derivative (III) may couple with alkyne in good yields by the present preparation.

In Step 3, a compound of formula (Ia-A) or (Ib-A) may be selectively prepared by the adjustment of amounts of the palladium catalyst to a compound of formula (III). In the preparation of a compound of formula (Ib-A), a compound of formula (Ib-A) may be produced in situ of Step 3, and hence, the next Step 4 may be skipped.

In Step 4 of the above Scheme A, the alkyne adduct (V) obtained in Step 3 is cyclized. The cyclization of Step 4 may be preferably carried out in the presence of water, more preferably in the mixture of water/alcoholic solvent, water/acetonitrile, or water/acetone. The alcoholic solvent includes methanol, ethanol, isopropanol, n-propanol, butanol, etc. A preferable content ratio in the mixtures of water/alcoholic solvent, water/acetonitrile, and water/acetone is 2/1.

In Step 4, the desired naphthofuranedione derivatives may be produced without the need for conversion of amino group $NR^2R^3$ into hydroxyl group in the adduct (V). The cyclization step 4 of the present invention may be carried out without any acids.

In both preparations of compounds of formulae (Ia-A) and (Ib-A), the above Steps 3 and 4 may be combined in one-pot reaction.

The present invention may be carried out without the need for protection of hydroxyl group attached to the naphthoquinone ring in the above Steps 1 to 4, but said hydroxyl group may be optionally protected by the appropriate protective group and then the protective group may be deprotected at an appropriate step according to the conventional methods. The protective group includes THP or Ac.

Scheme B: Preparation of Tricyclic Compounds

[Chemical Formula 19]

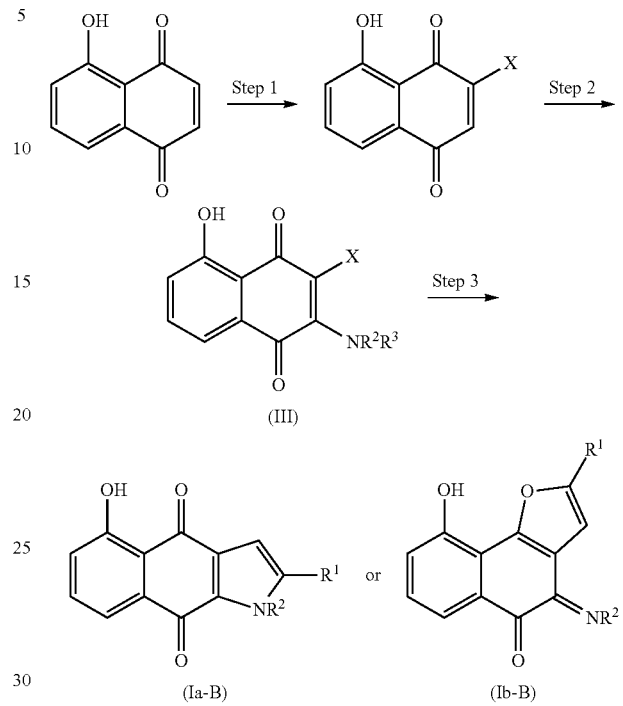

[In the Scheme, each symbol is the same as defined above.]

Step 1 in the above Scheme B may be, for example, carried out according to Tietze, et al., Chem. Eur. J., 2007, 13, 9939-9947. For example, to 5-hydroxynaphthalene-1,4-dione dissolved in an appropriate solvent is added bromine to give 3-bromojuglone in Step 1.

In Step 2 of Scheme B, for example, substituted juglone such as 3-bromojuglone obtained in Step 1 is reacted with an amine such as methylamine hydrochloride, and then thereto is added NBS, and the mixture is stirred. The resulting reaction solution is purified to give a compound of formula (III).

Step 3 may be carried out in the similar manner to the above Scheme A except for preferably using DMSO as the aprotic polar solvent.

In Scheme B, any steps corresponding to Step 4 of Scheme A may be unnecessary. Specifically, the compound (III) may react with alkyne in a coupling reaction, and then the ring-closure reaction may proceed in situ without purification or extraction of an intermediate to efficiently produce the desired compound (Ia-B) or (Ib-B).

Scheme C: Preparation of Tricyclic Compounds

[Chemical Formula 20]

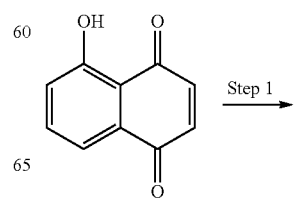

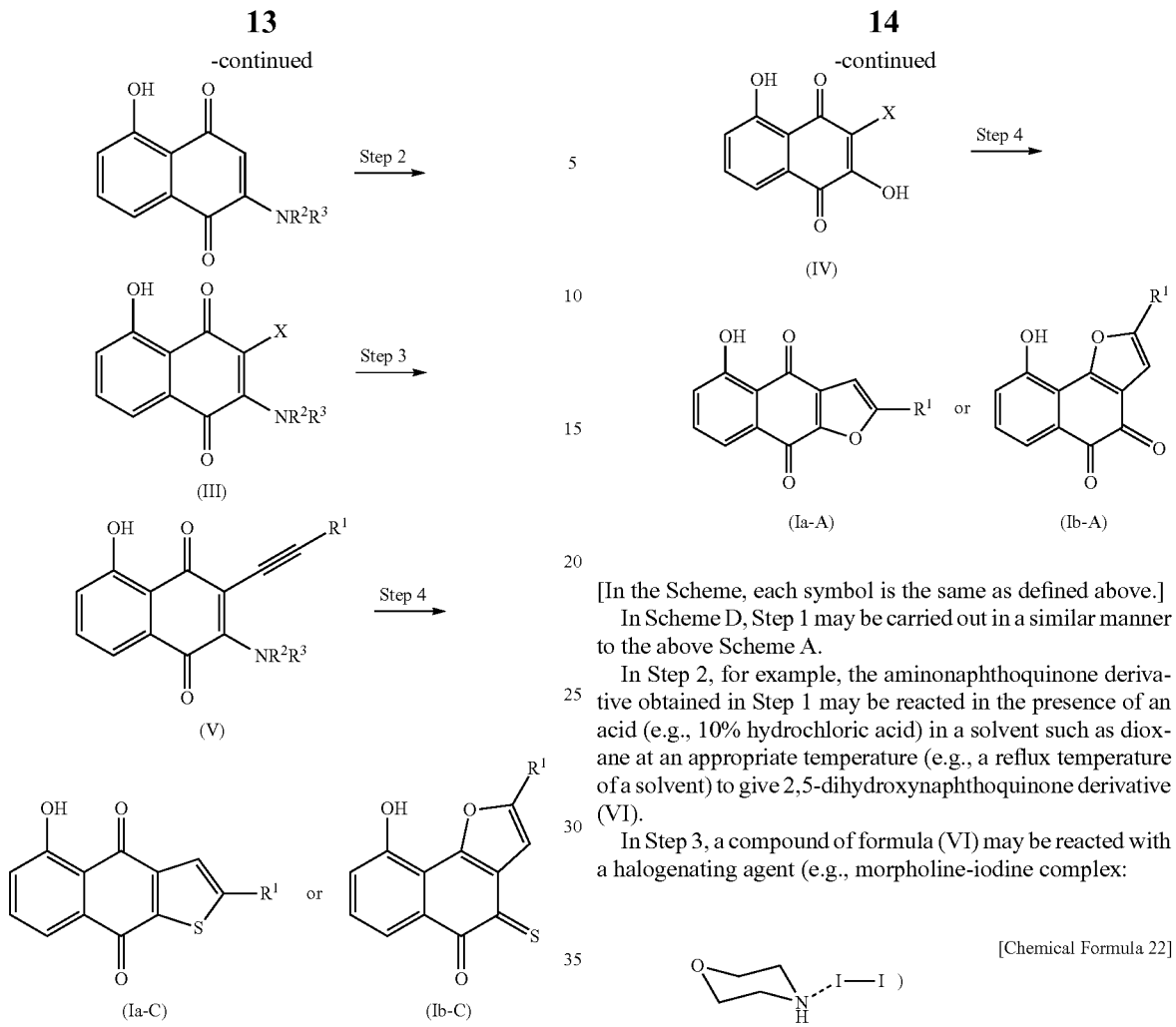

[In the Scheme, each symbol is the same as defined above.]

In Scheme C, Steps 1 to 3 may be carried out in a similar manner to the above Scheme A. In Step 4, the alkyne adduct (V) may react with a metal sulfide at 40° C. to 60° C., preferably 50° C. to produce a compound of formula (Ia-C) or (Ib-C). The metal sulfide includes sodium sulfide.

Scheme D: Preparation of Tricyclic Compounds

[Chemical Formula 21]

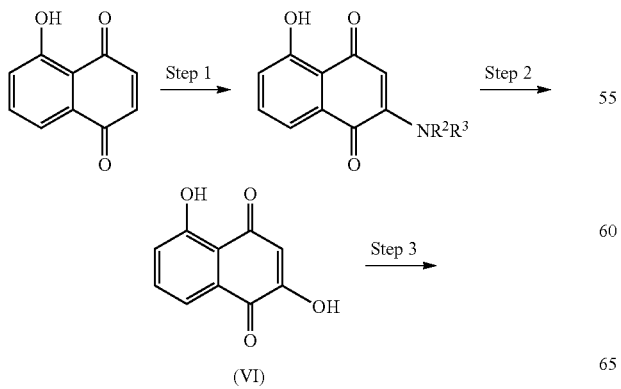

[In the Scheme, each symbol is the same as defined above.]

In Scheme D, Step 1 may be carried out in a similar manner to the above Scheme A.

In Step 2, for example, the aminonaphthoquinone derivative obtained in Step 1 may be reacted in the presence of an acid (e.g., 10% hydrochloric acid) in a solvent such as dioxane at an appropriate temperature (e.g., a reflux temperature of a solvent) to give 2,5-dihydroxynaphthoquinone derivative (VI).

In Step 3, a compound of formula (VI) may be reacted with a halogenating agent (e.g., morpholine-iodine complex:

[Chemical Formula 22]

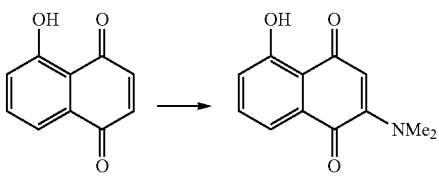

to give a compound of formula (IV).

In Step 4, a compound of formula (IV) may be reacted with the alkyne of formula (II) in the presence of a base, a copper catalyst and a palladium catalyst in an aprotic polar solvent to give a compound of formula (Ia-A) or (Ib-A). In the step, a preferable base and a preferable aprotic polar solvent include pyridine.

EXAMPLES

Preparation 1

Preparation of 2-dimethylaminojuglone

[Chemical Formula 23]

To a solution of 5-hydroxynaphthalene-1,4-dione (171 mg, 1 mmol) in toluene (5 mL) was added dimethylamine (0.75 mL, 2.0M solution in THF, 1.5 mmol) at −20° C. The mixture was stirred at −20° C. for 1 hour, and then thereto was added dimethylamine (0.75 mL, 2.0M solution in THF, 1.5 mmol). The mixture was stirred at −20° C. for additional 30 minutes, and then the solvent was evaporated under reduced pressure. The residue was isolated and purified by silica gel column chromatography (chloroform/ethyl acetate=20/1 (v/v)) to give 2-dimethylaminojuglone (87.2 mg, 40%) and 3-dimethylaminojuglone (28.8 mg, 13%).

2-Dimethylaminojuglone

Melting point: 147-148° C.

$^1$H-NMR (CDCl$_3$): δ 3.25 (s, 6H), 5.72 (s, 1H), 7.20 (dd, 1H, J=1.2, 8.3 Hz), 7.45-7.51 (m, 2H), 13.0 (s, 1H).

3-Dimethylaminojuglone $^1$H-NMR (CDCl$_3$): δ 3.23 (s, 6H), 5.84 (s, 1H), 7.15 (dd, 1H, J=3.7, 6.1 Hz), 7.56-7.59 (m, 2H), 11.9 (s, 1H).

Preparation 2

Preparation 2 of 2-dimethylaminojuglone

In the alternative method, 2-dimethylaminojuglone was prepared in the following scheme according to Tietze, et al., Chem. Eur. J., 2007, 13, 9939-9947 and Chaker, et al., Chem. Pharm. Bull., 1994, 42, 2238-2240.

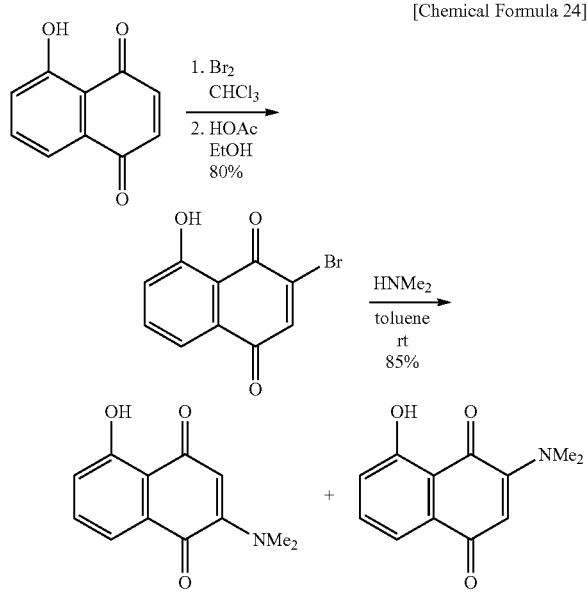

[Chemical Formula 24]

To a solution of 5-hydroxynaphthalene-1,4-dione (171 mg, 1 mmol) in chloroform was added bromine, and the mixture was stirred. Then, to the resulting mixture were added acetic acid and ethanol, and the mixture was stirred under reflux to give 3-bromojuglone (80%). To the resulting 3-bromojuglone was added dimethylamine, and the mixture was stirred in toluene at room temperature to give 2-dimethylaminojuglone and 3-dimethylaminojuglone (85%).

The yield ratio of the resulting 2-dimethylaminojuglone and 3-dimethylaminojuglone is 95:5.

Preparation 3

Preparation of 3-bromo-2-dimethylaminojuglone

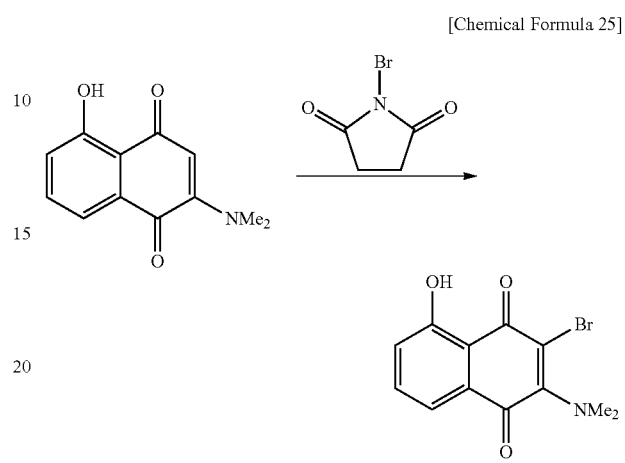

[Chemical Formula 25]

To a solution of 2-dimethylaminojuglone (500 mg, 2.3 mmol) in DMF (15 ml) was added a solution of NBS (491 mg, 2.76 mmol) in DMF (6 ml) at room temperature over 5 minutes, and the mixture was stirred for 20 minutes. The reaction was quenched by the addition of iced water, and extracted with chloroform. The organic layer was washed with water and brine, dried over sodium sulfate, filtered, and then the solvent was evaporated under reduced pressure to give 3-bromo-2-dimethylaminojuglone (656 mg, 96%) as a purple solid. $^1$H-NMR (CDCl$_3$): δ 3.29 (s, 6H), 7.22 (dd, 1H, J=1.8, 7.8 Hz), 7.49-7.55 (m, 2H), 12.48 (s, 1H).

Preparation 4

Preparation of 3-bromo-5-hydroxy-2-(methylamino)naphthalene-1,4-dione

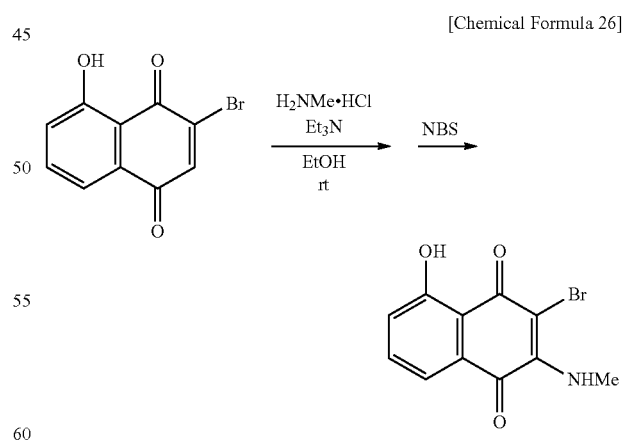

[Chemical Formula 26]

To a solution of 2-bromo-8-hydroxy-1,4-naphthalenedione (253 mg, 1.0 mmol) obtained according to Chem. Eur. J. 2007, 13, 9939-9947 and methylamine hydrochloride (68 mg, 1.0 mmol) in ethanol (8.0 mL) was added triethylamine (0.30 mL, 2.2 mmol) at room temperature, and the reaction solution was stirred for 1 day. The disappearance of the starting materials was confirmed by thin layer chromatography (TLC), and then to the reaction solution was added NBS (267 mg, 1.5 mmol) with cooling by iced water. The mixture was stirred for additional 30 minutes. The reaction solution was concentrated, and purified by silica gel column chromatography (hexane/ethyl acetate=10/1) to give the titled compound as a brown column crystal (250 mg, 89% yield, mp 159-160° C.).

rf (hexane/EtOAc=4/1)=0.40.

$^1$H-NMR (CDCl$_3$): 3.48 (3H, d, J=6.5 Hz); 7.26 (1H, dd, J=1.0, 8.0 Hz), 7.48 (1H, dd, J=7.5, 8.0 Hz), 7.59 (1H, dd, J=1.0, 7.5 Hz).

$^{13}$C-NMR (CDCl$_3$, 50° C.): 33.0, 114.2, 119.7, 125.9, 129.9, 134.2, 143.3, 147.8, 161.0, 179.4, 182.1.

IR (KBr): 3325, 1674, 1605, 1551, 1520, 1466, 1412, 1362, 1293, 1231, 1165, 1111, 829, 756.

LRMS (ESI) m/z: 282, 284 [M+H]$^+$. HRMS (ESI) m/z: [M+H]$^+$[C$_{11}$H$_9$NO$_3$Br]$^+$ Calculated 281.9766, 283.9745; Observed 281.9729, 283.9713.

Preparations 5 to 13

The following compounds of Preparations 5 to 13 are prepared with proper modifications of Preparations 1 to 4 according to the conventional methods in the art.

TABLE 1

| Preparation No. | Chemical Structure |
| --- | --- |
| 5 | 5-hydroxy-3-bromo-2-(NHMe)-1,4-naphthoquinone |
| 6 | 5-hydroxy-3-bromo-2-(NH-CH₂-NO₂)-1,4-naphthoquinone |
| 7 | 5-hydroxy-3-bromo-2-(NHAc)-1,4-naphthoquinone |
| 8 | 5-hydroxy-3-bromo-2-(NEt₂)-1,4-naphthoquinone |
| 9 | 5-hydroxy-3-iodo-2-(NMe₂)-1,4-naphthoquinone |
| 10 | 5-hydroxy-3-bromo-2-(N(Me)-CH₂-NO₂)-1,4-naphthoquinone |
| 11 | 5-hydroxy-3-bromo-2-(N(Me)-CH₂-SO₃H)-1,4-naphthoquinone |
| 12 | 5-hydroxy-3-bromo-2-(N(Me)-CH₂-CN)-1,4-naphthoquinone |
| 13 | 5-hydroxy-3-bromo-2-(N(Me)-Ac)-1,4-naphthoquinone |

Preparation 14

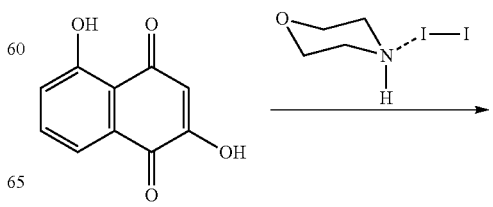

[Chemical Formula 27]

-continued

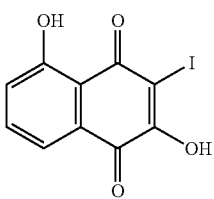

To a solution of 2,5-dihydroxynaphthalene-1,4-dione (100 mg, 0.53 mmol) in a distilled water (5 ml) was added potassium carbonate (218 mg, 1.58 mmol), and the mixture was stirred at room temperature. To the reaction solution was added morpholine-iodine complex (223 mg, 0.66 mmol) every 15 minutes over 2 hours. After the completion of the addition of the morpholine-iodine complex, the mixture was stirred for additional 30 minutes. The reaction was quenched by the addition of 25% phosphoric acid, and stirred for 10 minutes. The reaction solution was extracted with ethyl acetate, and the organic layer was washed with water and brine, dried over sodium sulfate and concentrated under reduced pressure to give 2,5-dihydroxy-3-iodonaphthalene-1,4-dione (156 mg, 94%).

$^1$H-NMR (CDCl$_3$): δ 7.28 (dd, 1H, J=1.1, 8.4 Hz), 7.54 (dd, 1H, J=7.5, 8.4 Hz), 7.66 (dd, 1H, J=1.1, 7.5 Hz), 12.08 (s, 1H).

Example 1

Alkyne Addition of 3-bromo-2-dimethylaminojuglone

[Chemical Formula 28]

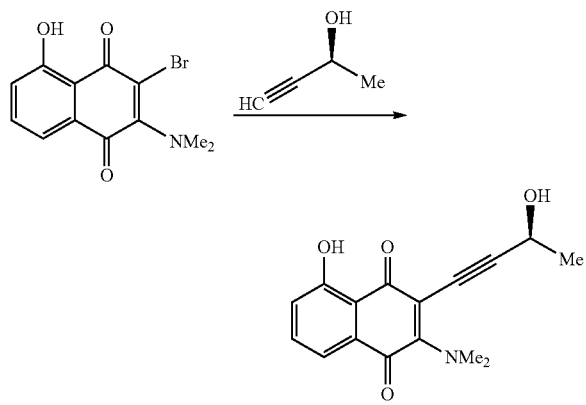

A solution of copper (I) oxide (available from Wako Pure Chemical Industries, Ltd., 144 mg, 1.01 mmol) and (S)-(−)-3-butyn-2-ol (available from Tokyo Chemical Industry Co., Ltd., 798 μl, 10.1 mmol, >98% ee) in DMF (36 ml) and pyridine (15 ml) was stirred at room temperature for 2 hours. To the reaction mixture were added 3-bromo-2-dimethylaminojuglone (300 mg, 1.01 mmol), and a solution of palladium acetate (available from Tokyo Chemical Industry Co., Ltd., 6.8 mg, 3 mol %) in DMF (42 ml), and the mixture was stirred overnight. The reaction was quenched by the addition of iced water, and the reaction mixture was extracted with chloroform. The organic layer was washed with iced water and brine, dried over sodium sulfate, filtered, and then concentrated under reduced pressure and purified by silica gel column chromatography (eluent: hexane/ethyl acetate=6/1) to give 2-dimethylamino-3-(3-hydroxybut-1-yn-1-yl)juglone (220 mg, 76%) as a purple solid.

$^1$H-NMR (CDCl$_3$): δ 1.50 (d, 3H, J=6.6 Hz), 3.42 (s, 6H), 4.79 (q, 1H, J=6.6 Hz), 7.11 (dd, 1H, J=3.9, 5.7 Hz), 7.37-7.40 (m, 2H), 12.61 (s, 1H).

$^{13}$C-NMR (CDCl$_3$): 23.9, 45.3, 59.1, 77.2, 78.3, 102.9, 104.1, 114.4, 119.0, 124.6, 132.1, 134.5, 155.5, 160.4, 182.5, 187.8.

IR (KBr): 3468, 1670, 1624, 1547, 1474, 1385, 1196, 1152, 1069, 1045, 895, 777.

Melting point: 156-158° C.

LRMS (ESI) m/z: 284 [M−H]$^-$. HRMS (ESI) m/z: [M−H]$^-$ [C$_{16}$H$_{14}$NO$_4$]$^+$ Calculated 284.0923; Observed 284.0904.

Example 2

Preparation 1 of NQ801

[Chemical Formula 29]

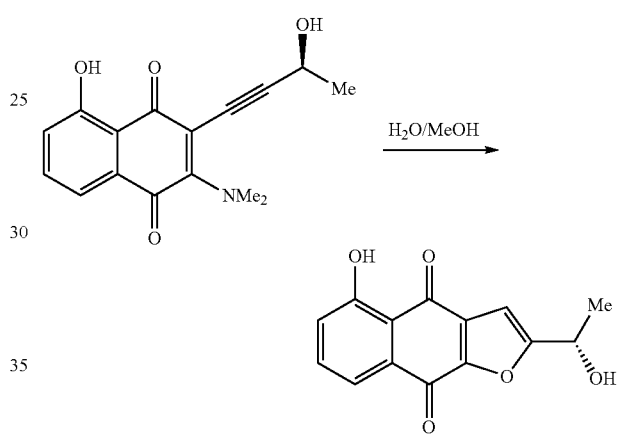

A solution of the compound (100 mg, 0.35 mmol) obtained in Example 1 in distilled water (120 ml) and methanol (60 ml) was stirred at 95° C. for 4 hours, and the reaction solution was cooled to room temperature, and then extracted with chloroform. The organic layer was washed with brine, dried over sodium sulfate, filtered, and then the solvent was evaporated under reduced pressure. Then, the residue was purified by silica gel column chromatography (eluent: hexane/ethyl acetate=10/1) to give (−)-2-(1-hydroxyethyl)-5-hydroxynaphtho[2,3-b]furane-4,9-dione (72 mg, 80%) as a yellow solid.

Example 3

Preparation 2 of NQ801

[Chemical Formula 30]

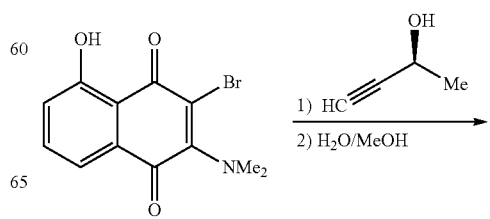

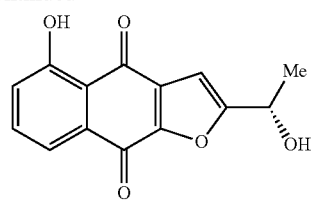 [SMILES: CCC(O)c1cc2c(s1)C(=O)c1cccc(O)c1C2=O]

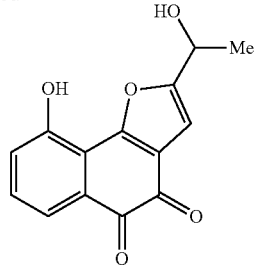

A solution of copper (I) oxide (available from Wako Pure Chemical Industries, Ltd., 48 mg, 0.34 mmol) and (S)-(−)-3-butyn-2-ol (available from Tokyo Chemical Industry Co., Ltd., 266 μl, 3.38 mmol, >98% ee) in DMF (12 ml) and pyridine (5 ml) was stirred at room temperature for 2 hours. To the reaction mixture were added 3-bromo-2-dimethylaminojuglone (100 mg, 0.34 mmol), and a solution of palladium acetate (available from Tokyo Chemical Industry Co., Ltd., 2.3 mg, 3 mol %) in DMF (14 ml), and the mixture was stirred overnight. The reaction was quenched by the addition of iced water, and the reaction mixture was extracted with chloroform. The organic layer was washed with iced water and brine, dried over sodium sulfate, filtered, and then concentrated under reduced pressure to give a crude product. A solution of the crude product in distilled water (120 ml) and methanol (60 ml) was stirred at 95° C. for 4 hours, and the reaction solution was cooled to room temperature, and then extracted with chloroform. The organic layer was washed with brine, dried over sodium sulfate, filtered, and then the solvent was concentrated under reduced pressure. Then, the residue was purified by silica gel column chromatography (eluent: hexane/ethyl acetate=10/1) to give (−)-2-(1-hydroxyethyl)-5-hydroxynaphtho[2,3-b]furane-4,9-dione (59 mg, 68%) as a yellow solid.

Melting point: 170° C.

$^{1}$H-NMR (CDCl$_3$): δ 1.66 (d, 3H, J=6.6 Hz), 2.23 (d, 1H, J=5.3 Hz), 5.05 (m, 1H), 6.85 (d, 1H, J=0.7 Hz), 7.28 (dd, 1H, J=1.2, 8.5 Hz), 7.62 (dd, 1H, J=7.6, 8.5 Hz), 7.76 (dd, 1H, J=1.2, 7.6 Hz) 12.18 (s, 1H).

$^{13}$C-NMR (CDCl$_3$): 21.5, 63.8, 103.4, 115.2, 120.0, 125.3, 131.0, 132.7, 136.3, 152.1, 162.3, 165.4, 172.7, 186.5.

$[\alpha]^{25}_D$ −23.5 (c 0.13, CH$_3$OH), 98% ee (HPLC, Daicel Chiralpak AD-H, hexane/i-PrOH=9/1, 1.0 mL/min, 254 nm, minor 22.3 min and major 24.5 min).

Example 4

Preparation of Ortho Quinone Derivatives

[Chemical Formula 31]

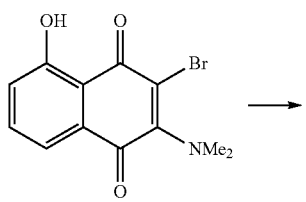

A solution of copper (I) oxide (available from Wako Pure Chemical Industries, Ltd., 48 mg, 0.34 mmol) and 3-butyn-2-ol (available from Tokyo Chemical Industry Co., Ltd., 263 μl, 3.38 mmol) in DMF (12 ml) and pyridine (5 ml) was stirred at room temperature for 2 hours. To the reaction mixture were added 3-bromo-2-dimethylaminojuglone (100 mg, 0.34 mmol), and a solution of palladium acetate (available from Tokyo Chemical Industry Co., Ltd., 4.6 mg, 6 mol %) in DMF (5 ml), and the mixture was stirred at 60° C. for 1 hour. Then, the mixture was stirred at 70° C. for 1 hour, and the reaction was quenched by the addition of iced water. The reaction mixture was extracted with chloroform, dried over sodium sulfate, filtered, and then concentrated under reduced pressure. The residue was purified by silica gel column chromatography (eluent: hexane/ethyl acetate=1/1) to give the desired compound (19 mg, 20%).

$^{1}$H-NMR (MeOD): δ 1.46 (d, 3H, J=6.6 Hz), 4.77 (m, 1H), 6.52 (s, 1H), 7.02 (dd, 1H, J=1.1, 8.3 Hz), 7.17 (dd, 1H, J=7.5, 8.3 Hz), 7.42 (dd, 1H, J=1.1, 7.5 Hz).

$^{13}$C-NMR (MeOD): 20.6, 62.7, 103.4, 121.1, 124.1, 125.6, 129.8, 131.5, 152.7, 160.1, 160.4, 162.9, 174.5, 180.4.

IR (KBr): 3443, 3124, 3082, 1670, 1665, 1587, 1319, 1288, 1080, 1067, 995, 939, 885, 826, 691, 669.

Melting point: >300° C.

LRMS (ESI) m/z: 257 [M−H]$^-$. HRMS (ESI) m/z: [M−H]$^-$ [C$_{14}$H$_9$O$_5$]$^-$ Calculated 257.0450; Observed 257.0432.

Examples 5 to 16

The following compounds of Examples 5 to 16 are prepared with proper modifications of Examples 1 to 3 according to the conventional methods in the art.

TABLE 2

| Example No. | Chemical Structure |
|---|---|
| 5 | (OH, O, naphthofuran-dione structure) |
| 6 | (OH, O, naphthofuran-dione with CH2OH) |

TABLE 2-continued

| Example No. | Chemical Structure |
|---|---|
| 7 | (5-hydroxy-naphtho[2,3-b]furan-4,9-dione with 1-hydroxypropyl substituent, Et, *OH) |
| 8 | (5-hydroxy-naphtho[2,3-b]furan-4,9-dione with 1-aminoethyl substituent, Me, *NH₂) |
| 9 | (5-hydroxy-naphtho[2,3-b]furan-4,9-dione with 1-methoxyethyl substituent, Me, *OMe) |
| 10 | (5-hydroxy-2-phenyl-naphtho[2,3-b]furan-4,9-dione) |
| 11 | (5-hydroxy-2-(4-hydroxyphenyl)-naphtho[2,3-b]furan-4,9-dione) |
| 12 | (5-hydroxy-2-(pyrrol-1-yl)-naphtho[2,3-b]furan-4,9-dione) |
| 13 | (5-hydroxy-naphtho[2,3-b]furan-4,9-dione-2-carbaldehyde) |

TABLE 2-continued

| Example No. | Chemical Structure |
|---|---|
| 14 | (5-hydroxy-naphtho[2,3-b]furan-4,9-dione-2-carboxamide) |
| 15 | (2-acetyl-5-hydroxy-naphtho[2,3-b]furan-4,9-dione) |
| 16 | (2-benzoyl-5-hydroxy-naphtho[2,3-b]furan-4,9-dione) |

In the above table, * refers to an asymmetric carbon atom.

Example 17

Preparation 1 of 1-methyl-2-(1-hydroxyethyl)-5-hydroxynaphtho[2,3-b]pyrrole-4,9-dione

[Chemical Formula 32]

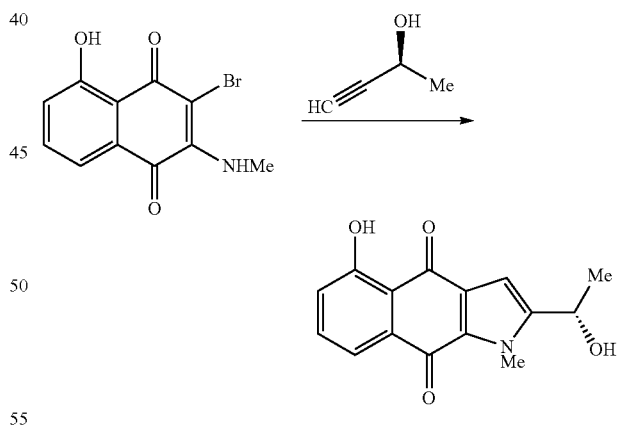

A solution of copper (I) oxide (available from Wako Pure Chemical Industries, Ltd., 71 mg, 0.5 mmol) and 3-butyn-2-ol (available from Tokyo Chemical Industry Co., Ltd., 389 μl, 5.0 mmol) in DMF (18 ml) and pyridine (7.4 ml) was stirred at room temperature for 2 hours. To the reaction mixture were added 3-bromo-2-monomethylaminojuglone (141 mg, 0.5 mmol), and a solution of palladium acetate (available from Tokyo Chemical Industry Co., Ltd., 3.4 mg, 3 mol %) in DMF (20 ml), and the mixture was stirred at room temperature overnight. The reaction was quenched by the addition of iced water, and the reaction mixture was extracted with chloroform. The organic layer was washed with iced water and brine, dried over sodium sulfate, filtered, and then concentrated under reduced pressure. The residue was purified by silica gel column chromatography (eluent: hexane/ethyl acetate=4/1) to give the desired compound (57 mg, 42%).

pale yellow needles, mp 219-220° C. (57 mg, 42% yield). rf (hexane/EtOAc=4/1)=0.20.

$^1$H-NMR (CDCl$_3$): 1.68 (3H, d, J=6.5 Hz), 1.98 (1H, d, J=7.5 Hz), 4.11 (3H, s), 4.93 (1H, dt, J=6.5, 7.5 Hz), 6.65 (1H, s), 7.17 (1H, dd, J=1.0, 8.5 Hz), 7.53 (1H, dd, J=7.5, 8.5 Hz), 7.63 (1H, dd, J=1.0, 7.5 Hz).

$^{13}$C-NMR (CDCl$_3$): 22.1, 33.4, 62.0, 105.1, 115.4, 119.2, 124.1, 126.8, 131.8, 134.3, 135.4, 145.4, 162.0, 175.7, 186.7.

IR (KBr): 3530, 1630, 1458, 1374, 1352, 1219, 1080.

LRMS (ESI) m/z: 270 [M–H]$^-$. HRMS (ESI) m/z: [M–H]$^-$ [C$_{15}$H$_{13}$NO$_4$]$^-$ Calculated 270.0766; Observed 270.0757.

Example 18

Preparation 2 of 1-methyl-2-(1-hydroxyethyl)-5-hydroxynaphtho[2,3-b]pyrrole-4,9-dione

[Chemical Formula 33]

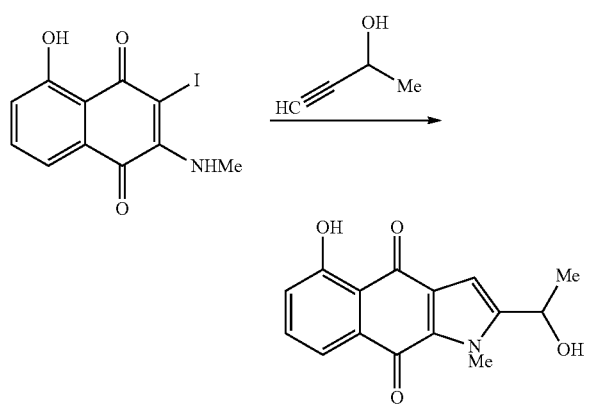

A solution of copper (I) oxide (available from Wako Pure Chemical Industries, Ltd., 22 mg, 0.15 mmol) and 3-butyn-2-ol (available from Tokyo Chemical Industry Co., Ltd., 120 µl, 1.52 mmol) in DMF (5 ml) and pyridine (2.3 ml) was stirred at room temperature for 2 hours. To the reaction mixture were added 3-iodo-2-monomethylaminojuglone (50 mg, 0.15 mmol), and a solution of palladium acetate (available from Tokyo Chemical Industry Co., Ltd., 1.0 mg, 3 mol %) in DMF (4 ml), and the mixture was stirred at 80° C. for 1 hour. The reaction was quenched by the addition of iced water, and the reaction mixture was extracted with chloroform. The organic layer was washed with iced water and brine, dried over sodium sulfate, filtered, and then concentrated under reduced pressure. The residue was purified by silica gel column chromatography (eluent: hexane/ethyl acetate=4/1) to give the desired compound (33 mg, 80%).

pale yellow needles, mp 219-220° C. (33 mg, 80% yield). rf (hexane/EtOAc=4/1)=0.20.

$^1$H-NMR (CDCl$_3$): 1.68 (3H, d, J=6.5 Hz), 1.98 (1H, d, J=7.5 Hz), 4.11 (3H, s), 4.93 (1H, dt, J=6.5, 7.5 Hz), 6.65 (1H, s), 7.17 (1H, dd, J=1.0, 8.5 Hz), 7.53 (1H, dd, J=7.5, 8.5 Hz), 7.63 (1H, dd, J=1.0, 7.5 Hz).

$^{13}$C-NMR (CDCl$_3$): 22.1, 33.4, 62.0, 105.1, 115.4, 119.2, 124.1, 126.8, 131.8, 134.3, 135.4, 145.4, 162.0, 175.7, 186.7.

IR (KBr): 3530, 1630, 1458, 1374, 1352, 1219, 1080.

LRMS (ESI) m/z: 270 [M–H]$^-$. FIRMS (ESI) m/z: [M–H]$^-$ [C$_{15}$H$_{13}$NO$_4$]$^-$ Calculated 270.0766; Observed 270.0757.

Example 19

Preparation of (S)-5-hydroxy-2-(1-hydroxyethyl)-1H-benzo[f]indole-4,9-dione

[Chemical Formula 34]

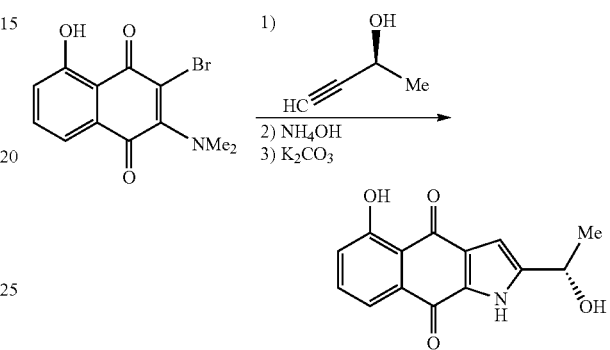

A solution of copper (I) oxide (available from Wako Pure Chemical Industries, Ltd., 48 mg, 0.34 mmol) and (S)-(–)-3-butyn-2-ol (available from Tokyo Chemical Industry Co., Ltd., 266 µl, 3.38 mmol) in DMF (12 ml) and pyridine (5 ml) was stirred at room temperature for 2 hours. To the reaction mixture were added 3-bromo-2-dimethylaminojuglone (100 mg, 0.34 mmol), and a solution of palladium acetate (available from Tokyo Chemical Industry Co., Ltd., 2.3 mg, 3 mol %) in DMF (14 ml), and the mixture was stirred overnight. The reaction was quenched by the addition of iced water, and the reaction mixture was extracted with chloroform. The organic layer was washed with iced water and brine, dried over sodium sulfate, filtered, and then concentrated under reduced pressure to give a crude product. To a solution of the crude product in NMP (20 ml) was added 28% ammonia water (available from Wako Pure Chemical Industries, Ltd., 208 µl, 2.57 mmol), and the mixture was stirred at 80° C. for 1 hour, and then thereto was added anhydrous potassium carbonate (available from Wako Pure Chemical Industries, Ltd., 35 mg, 0.26 mmol). The mixture was stirred at 80° C. for 30 minutes. To the reaction solution was added additional anhydrous potassium carbonate (available from Wako Pure Chemical Industries, Ltd., 248 mg, 1.80 mmol), and the mixture was stirred at 100° C. for 3 hours. The reaction solution was extracted with chloroform, and the organic layer was washed with 3M hydrochloric acid, water and brine, dried over sodium sulfate, filtered, and then the solvent was concentrated under reduced pressure. The residue was purified by silica gel column chromatography (eluent: hexane/ethyl acetate=2/1) to give (S)-5-hydroxy-2-(1-hydroxyethyl)-1H-benzo[f]indole-4,9-dione (20 mg, 23%) as a yellow solid.

$^1$H-NMR (CDCl$_3$): δ 1.64 (d, 3H, J=6.5 Hz), 5.08 (m, 1H), 6.58 (dd, 1H, J=0.8, 2.3 Hz), 7.21 (dd, 1H, J=1.2, 8.3 Hz), 7.54 (dd, 1H, J=7.5, 8.3 Hz), 7.68 (dd, 1H, J=1.2, 7.5 Hz) 12.63 (s, 1H).

IR (KBr): 3575, 1623, 1458, 1377, 1254, 1204, 1099, 1034, 764.

LRMS (ESI) m/z: 256 [M−H]−. FIRMS (ESI) m/z: [M−H]− [C$_{14}$H$_{10}$NO$_4$]− Calculated 256.0610; Observed 256.0604.

Example 20

Preparation 1 of 2-(1-hydroxyethyl)-5-hydroxynaphtho[2,3-b]thiophene-4,9-dione

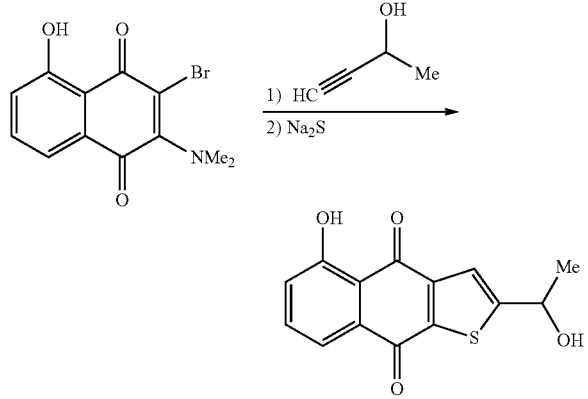

[Chemical Formula 35]

A solution of copper (I) oxide (available from Wako Pure Chemical Industries, Ltd., 24 mg, 0.167 mmol) and 3-butyn-2-ol (available from Tokyo Chemical Industry Co., Ltd., 133 μl, 1.69 mmol) in DMF (6 ml) and pyridine (2.5 ml) was stirred at room temperature for 2 hours. To the reaction mixture were added 3-bromo-2-dimethylaminojuglone (50 mg, 0.167 mmol), and a solution of palladium acetate (available from Tokyo Chemical Industry Co., Ltd., 1.1 mg, 3 mol %) in DMF (7 ml), and the mixture was stirred overnight. The reaction was quenched by the addition of iced water, and the reaction mixture was extracted with chloroform. The organic layer was washed with iced water and brine, dried over sodium sulfate, filtered, and then concentrated under reduced pressure to give a crude product. To a solution of the crude product in methanol (8 ml) and distilled water (100 μl) was added anhydrous sodium sulfide (available from Wako Pure Chemical Industries, Ltd., 26 mg, 0.334 mmol), and the mixture was stored at room temperature overnight. The reaction solution was quenched by an aqueous ammonium chloride solution, and extracted with ethyl acetate. The organic layer was washed with water and brine, dried over sodium sulfate, filtered, and then the solvent was concentrated under reduced pressure. The residue was purified by silica gel column chromatography (eluent: hexane/ethyl acetate=10/1) to give 2-(1-hydroxyethyl)-5-hydroxynaphtho[2,3-b]thiophene-4,9-dione (21 mg, 46%) as a yellow solid.

pale yellow needles, mp>193° C. (dec.). rf (CH$_2$Cl$_2$ only)= 0.20.

[α]$^{25}_D$−18.0 (c 0.15, CH$_3$OH), >99% ee (HPLC, Daicel Chiralpak AD-H, hexane/i-PrOH=9/1, 1.0 mL/min, 254 nm, minor 23.4 min and major 27.7 min).

$^1$H-NMR (CDCl$_3$): 1.67 (3H, d, J=7.0 Hz), 2.27 (1H, d, J=4.5 Hz), 5.22 (1H, dt, J=4.5, 7.0 Hz), 7.27 (1H, dd, J=1.0, 7.5 Hz), 7.50 (1H, s), 7.62 (1H, dd, J=7.5, 8.5 Hz), 7.76 (1H, dd, J=1.0, 7.5 Hz).

$^{13}$C-NMR (DMSO): 25.9, 65.2, 116.0, 119.7, 121.1, 124.9, 134.0, 137.1, 142.7, 143.2, 162.1, 164.6, 177.3, 185.2.

IR (KBr): 3275, 3187, 1649, 1632, 1451, 1288, 831, 752, 702.

LRMS (ESI) m/z: 273 [M−H]−. HRMS (ESI) m/z: [M−H]− [C$_{14}$H$_9$O$_4$S]− Calculated 273.0222; Observed 273.0216.

$^1$H-NMR (CDCl$_3$/MeOD): δ 1.64 (d, 1H, J=6.5 Hz), 5.16 (q, 1H, J=6.5 Hz), 7.27 (dd, 1H, J=0.94, 8.4 Hz), 7.49 (s, 1H), 7.62 (dd, 1H, J=7.5, 8.4 Hz), 7.76 (dd, 1H, J=0.94, 7.5 Hz), 12.34 (s, 1H).

Examples 21 to 32

The following compounds of Examples 21 to 32 are prepared with proper modifications of Example 20 according to the conventional methods in the art.

TABLE 3

| Example No. | Chemical Structure |
|---|---|
| 21 | ![structure] |
| 22 | ![structure] |
| 23 | ![structure] |
| 24 | ![structure] |
| 25 | ![structure] |

TABLE 3-continued

| Example No. | Chemical Structure |
|---|---|
| 26 | 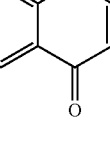 |
| 27 | 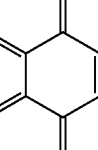 |
| 28 | 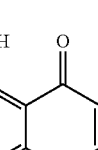 |
| 29 | 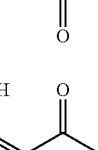 |
| 30 | 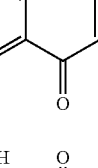 |
| 31 | 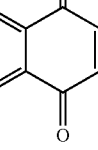 |
| 32 | 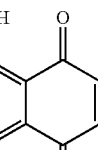 |

In the above table, * refers to an asymmetric carbon atom.

Example 33

[Chemical Formula 36]

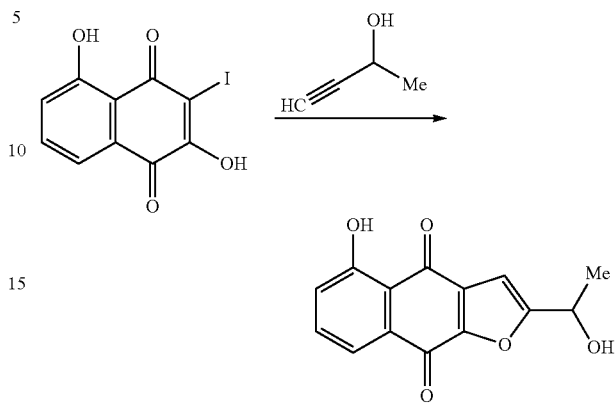

To a solution of 2,5-dihydroxy-3-iodonaphthalene-1,4-dione (30 mg, 0.095 mmol) in pyridine (3.5 ml) were added copper oxide (I) (13.5 mg, 0.095 mmol), 3-butyn-2-ol (75 μl, 0.949 mmol) and dichlorobis(triphenylphosphine)palladium (2 mg, 3 mol %), and the mixture was stirred at 80° C. of the reaction temperature for 30 minutes. The reaction solution was cooled to room temperature, and then the reaction was quenched by the addition of 2M hydrochloric acid. The reaction solution was extracted with chloroform. The organic layer was washed with ice water and brine, dried over sodium sulfate and concentrated under reduced pressure. The residue was purified by silica gel column chromatography (eluent: hexane/ethyl acetate=4/1) to give 2-(1-hydroxyethyl)-5-hydroxynaphtho[2,3-b]furan-4,9-dione (17.2 mg, 70%) as a yellow solid.

$^1$H-NMR (CDCl$_3$): δ 1.66 (d, 3H, J=6.6 Hz), 2.23 (d, 1H, J=5.3 Hz), 5.05 (m, 1H), 6.85 (d, 1H, J=0.7 Hz), 7.28 (dd, 1H, J=1.2, 8.5 Hz), 7.62 (dd, 1H, J=7.6, 8.5 Hz), 7.76 (dd, 1H, J=1.2, 7.6 Hz) 12.18 (s, 1H).

$^{13}$C-NMR (CDCl$_3$): 21.5, 63.8, 103.4, 115.2, 120.0, 125.3, 131.0, 132.7, 136.3, 152.1, 162.3, 165.4, 172.7, 186.5.

Preparation of NQ801

[Chemical Formula 37]

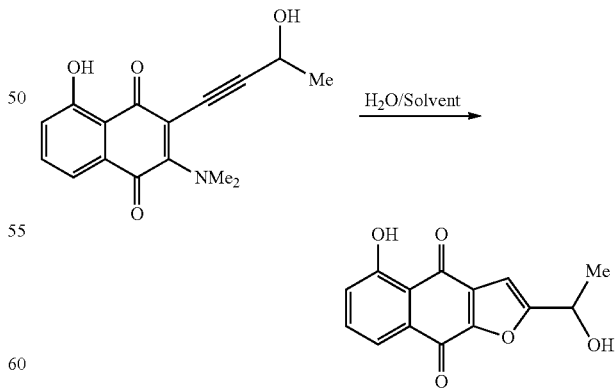

Example 34

A solution of the compound obtained in Example 1 (30 mg, 0.105 mmol) in a distilled water (20 ml) and butanol (10 ml)

was stirred at 120° C. overnight. The reaction solution was cooled to room temperature, and then extracted with ethyl acetate. The organic layer was washed with water and brine, dried over sodium sulfate, filtered, and concentrated under reduced pressure, and then the residue was purified by silica gel column chromatography (eluent: hexane/ethyl acetate=6/1) to give 2-(1-hydroxyethyl)-5-hydroxynaphtho[2,3-b]furan-4,9-dione (16.4 mg, 61%).

Example 35

A solution of the compound obtained in Example 1 (30 mg, 0.105 mmol) in a distilled water (20 ml) and ethanol (10 ml) was stirred at 100° C. for 5 hours. The reaction solution was cooled to room temperature, and then extracted with ethyl acetate. The organic layer was washed with water and brine, dried over sodium sulfate, filtered, and concentrated under reduced pressure, and then the residue was purified by silica gel column chromatography (eluent: hexane/ethyl acetate=6/1) to give 2-(1-hydroxyethyl)-5-hydroxynaphtho[2,3-b]furan-4,9-dione (14.8 mg, 55%).

Example 36

A solution of the compound obtained in Example 1 (30 mg, 0.105 mmol) in a distilled water (20 ml) and acetonitrile (10 ml) was stirred at 100° C. overnight. The reaction solution was cooled to room temperature, and then extracted with ethyl acetate. The organic layer was washed with water and brine, dried over sodium sulfate, filtered, and concentrated under reduced pressure, and then the residue was purified by silica gel column chromatography (eluent: hexane/ethyl acetate=6/1) to give 2-(1-hydroxyethyl)-5-hydroxynaphtho[2,3-b]furan-4,9-dione (11 mg, 41%).

Example 37

A solution of the compound obtained in Example 1 (30 mg, 0.105 mmol) in a distilled water (20 ml) and acetone (10 ml) was stirred at 100° C. overnight. The reaction solution was cooled to room temperature, and then extracted with ethyl acetate. The organic layer was washed with water and brine, dried over sodium sulfate, filtered, and concentrated under reduced pressure, and then the residue was purified by silica gel column chromatography (eluent: hexane/ethyl acetate=6/1) to give 2-(1-hydroxyethyl)-5-hydroxynaphtho[2,3-b]furan-4,9-dione (10 mg, 37%).

Comparative Example 1

[Chemical Formula 38]

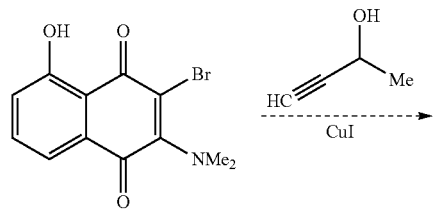

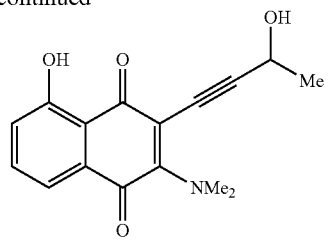

A coupling reaction was tried according to Nonpatent Document 4. To a solution of copper iodide (available from Wako Pure Chemical Industries, Ltd., 30 mg, 0.16 mmol) and 3-Butyn-2-ol (available from Tokyo Chemical Industry Co., Ltd., 11 μl, 0.15 mmol) in DMSO (500 μl) and chloroform (350 μl) were added triethylamine (available from Tokyo Chemical Industry Co., Ltd., 18 μl, 0.13 mmol), 3-bromo-2-dimethylaminojuglone (30 mg, 0.1 mmol) and bis(triphenylphosphine)palladium (II) dichloride (available from Tokyo Chemical Industry Co., Ltd., 300 μg, 0.43 mol %), and the mixture was stirred overnight. However, the desired compound was not obtained.

INDUSTRIAL APPLICABILITY

The present invention provides a novel and selective preparation of tricyclic compounds wherein the number of reaction steps is reduced compared to the conventional methods, which is useful for the selective preparation of tricyclic compounds.

The invention claimed is:

1. A process for preparing selectively one of a compound (Ia) and a compound (Ib) represented by following formula (Ia) and formula (Ib), respectively, over the other compound:

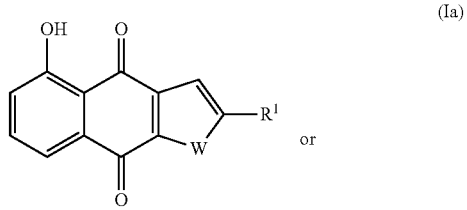

(Ia)

or

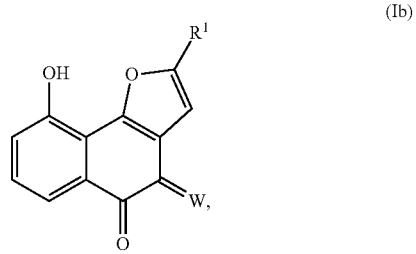

(Ib)

wherein $R^1$ is selected from the group consisting of hydrogen; $C_{1-6}$ alkyl optionally substituted by hydroxy, $C_{1-6}$ alkoxy, or amino; $C_{5-10}$ aryl optionally substituted by hydroxy, $C_{1-6}$ alkoxy, or amino; 5- to 10-membered saturated or unsaturated heterocycle optionally substituted by hydroxy, $C_{1-6}$ alkoxy, or amino; CHO; $CONH_2$; $C_{1-6}$ alkylcarbonyl optionally substituted by hydroxy, $C_{1-6}$ alkoxy, or amino; and $COC_{5-10}$ aryl optionally substituted by hydroxy, $C_{1-6}$ alkoxy, or amino, and W is O or S, the method comprising:
step (a) in which a compound (II) represented by following formula (II):

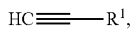
(II)

wherein $R^1$ is defined above,
is reacted in the presence of a base, a copper catalyst, and a palladium catalyst, in an aprotic polar solvent with a compound (III) represented by following formula (III):

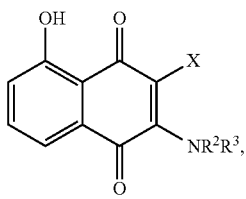
(III)

wherein $R^2$ is selected from the group consisting of hydrogen; $C_{1-6}$ alkyl optionally substituted by nitro, sulfo, cyano, acetyl, or $C_{5-10}$ aryl; $COC_{1-6}$ alkyl; and $COC_{5-10}$ aryl optionally substituted by nitro, sulfo, cyano, or acetyl, $R^3$ is selected from the group consisting of hydrogen; $C_{1-6}$ alkyl optionally substituted by nitro, sulfo, cyano, acetyl, or $C_{5-10}$ aryl; $COC_{1-6}$ alkyl; and $COC_{5-10}$ aryl optionally substituted by nitro, sulfo, cyano, or acetyl, and X is halogen selected from the group consisting of chlorine, bromine, and iodine; or $OSO_2CF_3$, wherein the compound (Ia) is formed selectively by including the palladium catalyst in an amount of less than a determining amount, and the compound (Ib) is formed selectively by including the palladium catalyst in an amount of no less than the determining amount.

2. The process of claim 1, wherein the copper catalyst used in step (a) is copper (I) oxide.

3. The process of claim 2, wherein $R^1$ is hydroxy-substituted $C_{1-6}$ alkyl.

4. The process of claim 1, which further comprises step (b) in which a compound (V) represented by following formula (V):

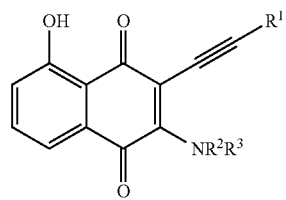
(V)

is obtained from the compound (III) in the step (a) and is cyclized.

5. The process of claim 1, wherein the less than the determining amount of the palladium catalyst for forming the compound (Ia):

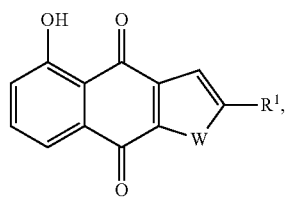 [SMILES: O=C1c2cccc(O)c2C(=O)c2cc(-c3ccccc3)sc21]
(Ia)

selectively is less than 5 mol % relative to the compound (III).

6. The process of claim 1, wherein the no less than the determining amount of the palladium catalyst for forming the compound (Ib):

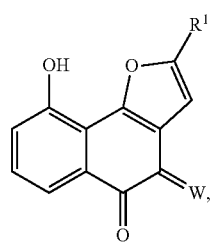
(Ib)

selectively is 5 mol % or more relative to the compound (III).

7. The process of claim 1, wherein both the base and the aprotic polar solvent used in the step (a) are pyridine.

* * * * *